(12) United States Patent
Holschen

(10) Patent No.: US 7,560,465 B2
(45) Date of Patent: Jul. 14, 2009

(54) COMPOSITIONS AND METHODS FOR DELIVERY OF CAFFEINE

(76) Inventor: Richard Holschen, 1421 Evergreen Dr., River Falls, WI (US) 54022

( * ) Notice: Subject to any disclaimer, the term of this patent is extended or adjusted under 35 U.S.C. 154(b) by 629 days.

(21) Appl. No.: 11/094,016

(22) Filed: Mar. 31, 2005

(65) Prior Publication Data

US 2006/0222611 A1    Oct. 5, 2006

(51) Int. Cl.
*A61Q 1/04* (2006.01)
*A61K 31/522* (2006.01)

(52) U.S. Cl. .................... 514/263.34; 424/64

(58) Field of Classification Search .............. 424/64; 514/263.34
See application file for complete search history.

(56) References Cited

U.S. PATENT DOCUMENTS

| | | | |
|---|---|---|---|
| 4,699,780 A * | 10/1987 | Jennings et al. ............. 424/60 |
| 5,382,436 A * | 1/1995 | Potts ....................... 424/489 |
| 5,554,379 A | 9/1996 | Cuca et al. |
| 5,554,380 A | 9/1996 | Cuca et al. |
| 5,670,163 A | 9/1997 | Cuca et al. |
| 5,858,391 A | 1/1999 | Cuca et al. |
| 5,900,416 A * | 5/1999 | Markson ................... 424/728 |
| 6,190,673 B1 * | 2/2001 | Guskey et al. ............. 424/401 |
| 6,485,732 B1 | 11/2002 | Bekele |
| 6,488,947 B1 | 12/2002 | Bekele |
| 6,491,934 B1 | 12/2002 | Bekele |
| 6,491,935 B1 | 12/2002 | Bekele |
| 6,495,150 B2 | 12/2002 | Bekele |
| 6,565,865 B2 | 5/2003 | Bekele |
| 6,589,542 B2 | 7/2003 | Bekele |
| 6,607,737 B2 | 8/2003 | Bekele et al. |
| 6,613,341 B2 | 9/2003 | Motley et al. |
| 6,645,512 B2 | 11/2003 | Bekele |
| 6,713,075 B2 | 3/2004 | Bekele |
| 7,037,511 B1 * | 5/2006 | Gers-Barlag et al. ........ 424/401 |
| 2002/0098158 A1 * | 7/2002 | Singh ....................... 424/59 |
| 2005/0084506 A1 * | 4/2005 | Tachdjian et al. .......... 424/400 |

FOREIGN PATENT DOCUMENTS

GB        000005922 A1 * 10/1979 ................ 424/64

OTHER PUBLICATIONS

Nehlig, Astrid. Are we dependent upon coffee and caffeine? A review on Human and animal data. Jun. 1999, vol. 23, pp. 563-576 (article) Neuroscience And Biobehavioral Reviews [online]. Kidlington, Oxford, UK: Elsevier Science [retrieved Apr. 29, 2008]. Retrieved from Science Direct (online e-Journal database).*
Answers.com [online]. Search: "balm" (Apr. 19, 2005) [retrieved Apr. 28, 2008]. Retrieved from the internet <URL:http://www.answers.com/topic/balm>.*
Dias, M. et al., "Topical Delivery of Caffeine from Some Commercial Formulations," *International Journal of Pharmaceutics*, vol. 182, pp. 41-47 (1999).
Gupta, S., "New Delivery Systems for Topical Nutraceutical (Nutracosmetic) and Cosmeceutical Formulations," *Business Briefing: Global Cosmetics Manufacturing* (2004).

* cited by examiner

*Primary Examiner*—Raymond J Henley, III
(74) *Attorney, Agent, or Firm*—Christopher D. Gram

(57) ABSTRACT

Methods for delivery of caffeine, compositions including caffeine, and methods of making such compositions are disclosed. Generally, the method of delivering caffeine includes topically administering to a mucosal skin surface of a subject a dose of caffeine effective to increase alertness in the subject. The compositions generally include a lip balm base and caffeine. The methods of making the compositions generally include melting a lip balm base, dissolving caffeine in a solvent, adding the dissolved caffeine to the molten lip balm base, and allowing the lip balm base/caffeine mixture to cool.

20 Claims, No Drawings

COMPOSITIONS AND METHODS FOR DELIVERY OF CAFFEINE

BACKGROUND

Caffeine is a mild stimulant that may be found in the leaves, fruits, and/or seeds of many plants such as, for example, *Thea* species, *Camellia* species, *Theobroma cacao, Coffee arabica*, and *Cola* species. The most common sources of caffeine include coffee (e.g., seeds of *Coffee arabica*), tea (e.g., leaves of *Thea sinensis, Camellia sinensis*, etc.), cola soft drinks (e.g., extracts of the nuts of *Cola acuminata, Cola nitida*, etc.), chocolate (e.g., the seeds of *Theobroma cacao*), and over-the-counter medications.

Caffeine is recognized as having many physiological and/or pharmacological effects: it may, for example, stimulate the central nervous system, promote analgesia, temporarily increase metabolic function, relax smooth muscle, and/or act as a diuretic. Caffeine is a xanthine compound and, therefore, has been included in certain topical cosmetic products as an anti-cellulite agent. However, the efficacy of caffeine, whether ingested or applied topically, for managing cellulite is not confirmed.

The ability of caffeine to stimulate the central nervous system is one reason for the popularity of caffeine-containing beverages (e.g., coffee, tea, and/or caffeinated soft drinks). There are many reasons that people turn to caffeinated beverages and/or caffeine-containing stimulants products as to promote alertness. Recuperation from certain illnesses may leave one drowsy. Many jobs require a high level of alertness and/or overnight working hours in which drowsiness on the job may be dangerous to the worker and/or others (e.g., police officer, security guard, over-the-road truck driver, etc.). The demands of a school- or job-related deadline may force one to remain alert working or studying into the night. The use of caffeine to increase alertness typically involves ingesting a "dose" of caffeine so that it is absorbed into the bloodstream through the lining of the digestive tract.

A six-ounce cup of coffee can contain from about 40 milligrams (mg) to more than 150 mg of caffeine. A generally accepted "average" caffeine content for a cup of coffee is 100 mg, although many coffee-based drinks typically contain many times that amount. For example, espresso may contain 100 mg of caffeine per fluid ounce. Also, many popular coffee drinks are sold in sizes much larger than the generally accepted "average" six fluid ounce serving.

Certain soft drinks and energy drinks can contain from about 35 mg to about 80 mg of caffeine per serving and, like the coffee-based beverages just described, are often sold in sizes larger than a single serving. Chocolate can contain up to about 15 mg of caffeine per ounce. Certain over-the-counter stimulants contain 100 mg to 200 mg of caffeine.

Despite their popularity, ingestible forms of caffeine such as certain foods, caffeinated beverages, and ingestible over-the-counter medications may not be suitable for all instances in which one might desire to use caffeine to stay alert. For example, a food (e.g., chocolate) may be an undesirable vehicle for delivering caffeine because it may raise nutritional concerns, be messy, or for reasons of personal taste. As another example, caffeinated beverages and over-the-counter medications can require the co-ingestion of fluids, sometimes in large volume. When combined with the diuretic effect of caffeine, this can result in diuresis or an undesirable frequency of urination, particularly if one desires to remain alert in either an environment in which adequate facilities are unavailable or circumstances in which urination would be inconvenient.

Consequently, a need exists for alternative methods of delivering caffeine that do not require co-ingestion of liquids and/or are convenient, neat, and/or palatable.

SUMMARY

It has been found that application of a caffeine-containing formulation (e.g., a caffeinated lip balm) to a mucous membrane surface (e.g., lip skin) can deliver a dose of caffeine adequate to improve attentiveness. Consequently, in one embodiment, the present invention provides a lip balm that includes a lip balm base and caffeine. In certain embodiments, the lip balm can include from at least about 80 micrograms (µg) to at least about 400 milligrams of caffeine per gram (g) of lip balm base. In certain embodiments, the lip balm may further include at least one additive.

In another aspect, the present invention provides a method of making a lip balm. Generally, the method includes melting a lip balm base, dissolving a quantity of caffeine in a solvent, adding the dissolved caffeine to the molten lip balm base, and allowing the lip balm base/caffeine mixture to cool. In some embodiments, the quantity of caffeine may range from at least about 80 mg per kilogram (kg) of lip balm base to at least about 400 g per kg of lip balm base. In certain embodiments, the method may further include adding at least one additive to the molten lip balm base.

In yet another aspect, the invention provides a method of systemically delivering a dose of caffeine to a subject. Generally, the method includes topically administering to a mucosal membrane of the subject a dose of caffeine effective to increase alertness in the subject. In some embodiments, the mucosal membrane may include an oral lip. In certain embodiments, the dose of caffeine may be formulated in a lip balm.

Various other features and advantages of the present invention should become readily apparent with reference to the following detailed description, examples, and claims. In several places throughout the specification, guidance is provided through lists of examples. In each instance, the recited list serves only as a representative group and should not be interpreted as an exclusive list. Also, recitation of a numerical range by endpoints includes all numbers subsumed within that range (e.g., 1 to 5 includes 1, 1.5, 2, 2.75, 3, 3.80, 4, 5, etc.).

DETAILED DESCRIPTION OF ILLUSTRATIVE EMBODIMENTS OF THE INVENTION

The present invention provides a caffeinated formulation capable of being topically administered to a mucous membrane surface of the body. For example, one embodiment of the invention is a caffeinated lip balm that may be applied to the mucous membrane surface of lip skin. Thus, one can combine the standard benefits of a lip balm—protecting the lips from heat, cold, sun, wind, etc.—with providing a dose of caffeine sufficient to improve alertness. This may be particularly desirable for those who desire a temporary aid to remain alert but prefer to refrain from ingesting typical ingestible sources of caffeine. One may prefer to avoid such sources of caffeine, for reasons such as, for example, convenience, personal taste, and/or to avoid co-ingestion of liquid.

Some typical dietary sources of caffeine may be inconvenient and/or potentially messy to carry in some circumstances. Chocolate, for example, may melt easily. In contrast, typical lip balms require exposure to much higher temperatures than chocolate before they begin to melt. Caffeinated beverages may be susceptible to spilling and/or are stored in containers that may be inconvenient to carry while participating in certain activities. In contrast, lip balm may be packaged in a tube, pot, or covered tin that substantially prevents spilling. Moreover, typical lip balm tubes, pots, or tins are small and may be conveniently carried in even a small pocket.

Caffeine is a diuretic—it induces urination. Thus, co-ingestion of liquids (e.g., a caffeinated beverage or liquid to assist swallowing a caffeine-containing over-the-counter stimulant) in order to obtain an alertness-promoting dose of caffeine can exacerbate the diuretic effect of caffeine, causing one to experience a frequent and/or strong urge to urinate. In circumstances in which one desires to remain alert but in which urination is inconvenient or impossible (e.g., because adequate facilities are unavailable, one cannot be excused to use available facilities, and/or social or legal restrictions), it may be desirable to be able to obtain an alertness-promoting dose of caffeine without co-ingesting fluid.

Consequently, in one aspect, the present invention provides a lip balm that contains, generally, a lip balm base and caffeine. The amount of caffeine contained in the lip balm should be at least enough to provide a dose of caffeine effective to promote alertness when the lip balm is topically applied to the mucous membrane surface of lip skin. Such a dose may be, for example, the equivalent of a dose of caffeine that may be obtained by ingesting one of the various dietary or medicinal sources of caffeine described above. The caffeine content of such sources may range from about 1 mg (e.g., the caffeine content of a one ounce serving of some milk chocolates) to more than 100 mg (e.g., the caffeine content of some coffee drinks and some over-the-counter stimulant products). Thus, the total amount of caffeine contained within the lip balm may be approximately the intended dose per use (e.g., from about 1 mg to about 100 mg per dose) times the expected number of doses contained in the container of lip balm. Because the volume of lip balm may vary depending upon the size of the container in which the lip balm is stored, it is impractical to set forth the amount of caffeine that can be included in the lip balm for all potential applications. One of skill in the art, however, can readily formulate a lip balm capable of delivering a desired dose of caffeine per use.

In some embodiments, the amount of caffeine necessary to promote alertness may be less than the amount in one of the dietary sources described above. For example, a standard lip balm tube that includes 4.3 g of lip balm containing 1.4 mg of caffeine per gram of lip balm base (i.e., a total of about 6 mg caffeine per tube) can provide enough lip balm for more than one hundred applications—i.e., more than 100 doses of caffeine in an amount sufficient to promote alertness. Thus, a lip balm according to one embodiment of the invention may provide microgram quantity doses of caffeine that are effective to increase alertness.

Accordingly, in some embodiments, the lip balm may include caffeine in a concentration from at least 80 µg per gram of lip balm base to about 400 mg per gram of lip balm base, although in certain embodiments, the lip balm may include a concentration of caffeine outside of this range. In some embodiments, the lip balm may include at least about 1.4 mg of caffeine per gram of lip balm base. In other embodiments, the lip balm may include at least about 22 mg of caffeine per gram of lip balm base. In other embodiments, the lip balm may include at least about 44 mg of caffeine per gram of lip balm base. In still other embodiments, the lip balm may include at least about 400 mg of caffeine per gram of lip balm base.

The lip balm base may be any suitable lip balm base. A suitable lip balm base can be solid at room temperature (e.g., approximately 23° C.), but have a reasonably low melting point so that it can be easily melted for manufacture.

Many lip balm bases are known in the art. For example, some lip balm bases contain, generally, approximately 40% cosmetic grade oil that is liquid at room temperature (unless otherwise indicated, all percentages herein are weight/weight percentages), approximately 25% cosmetic grade oil that is solid at room temperature, approximately 20% cosmetic grade beeswax, and approximately 15% cosmetic grade oil that is brittle at room temperature.

Cosmetic grade oils that are liquid at room temperature include, for example, sweet almond oil, apricot kernel oil, avocado oil, grapeseed oil, hemp seed oil, macadamia oil, olive oil, and sunflower oil.

Cosmetic grade oils that are solid at room temperature include, for example, coconut oil, lanolin, palm oil, mango butter, and shea butter.

Cosmetic grade oils that are brittle at room temperature include, for example, cocoa butter and palm kernel oil.

In this general formulation, increasing the percentage of beeswax can increase the hardness of a lip balm base. Conversely increasing the percentage of oil that is liquid at room temperature can soften the lip balm base.

Alternatively, the lip balm base may include, for example, aloe barbadensis leaf extract, alumina, arachidyl propionate, butylated hydroxytoluene (BHT, a preservative), cetyl alcohol, colloidal silicon dioxide, carnauba wax, isopropyl lanolate, isopropyl myristate, lanolin, methylparaben, mineral oil, octyldodecanol, oleyl alcohol, paraffin, phenyl trimethicone, polyhydroxystearic acid, propylparaben, saccharin, silica, titanium dioxide, vitamin E acetate, and white wax.

As another example, the lip balm base may contain, for example, petroleum, lanolin, cocoa butter, and a mixture of waxes.

As another example, the lip balm base may contain beeswax, camphor, cetyl alcohol, cetyl palmitate, candelilla wax, lanolin, lanolin oil, methylparaben, mineral oil, ozokerite, paraffin, petrolatum, cocoa butter, polybutene, and propylparaben.

As another example, the lip balm base may include coconut oil, beeswax, sweet almond oil, peppermint oil, vitamin E, lanolin, comfrey root extract, and rosemary extract.

As another example, the lip balm base may include beeswax, coconut oil, sunflower oil, vitamin E, lanolin, peppermint oil, comfrey root extract, rosemary extract.

As another example, some lip balm bases can contain approximately 10% petrolatum, approximately 10% glycerol, approximately 3.4% silicone elastomer, approximately 64.3% cyclomethicone, approximately dimethicone copolyol, approximately 0.3% preservative, and approximately 7% ozokerite wax.

As yet another example, the lip balm base may be a commercially available lip balm base. Commercially available lip balm bases are available from numerous sources and the particular ingredients may vary considerably. For example, one commercially available lip balm base (The Chemistry Store, Pompano Beach, Fla.) lip balm base contain hydrogenated soybean oil, cocoa butter, shea butter, apricot kernel oil, sweet almond oil, vitamin E, and butylated hydroxytolune (BHT, a preservative).

Another commercially available lip balm base (Soap Crafters Co., Salt Lake City, Utah) contains avocado oil, beeswax, natural jojoba, and flavor. Yet another commercially available lip balm base (Rachel's Craft Supply, Gautier, Miss.) contains olive oil, carnauba wax, candelilla wax, and beeswax.

In one particular embodiment, the lip balm base is a commercially available lip balm base (Le Melange Home Fragrances, Wellington, Fla.) and includes hexyldecyl laurate, lexydecanol, ozokerite wax, dipropylene glycol dicaprylate-caprate, and isononanoate.

The lip balm may include one or more additives such as, for example, a colorant, a flavorant, a preservative, a skin penetration enhancer, a moisturizer, a vitamin, or a sweetener. As used herein, "a," "an," "the," "at least one," and "one or more" are used interchangeably. Thus, for example, a lip balm comprising "a" flavorant can be interpreted to mean that the lip balm includes at least one flavorant. Many suitable flavorants, sweeteners, and cosmetic grade additives are commercially available.

Some suitable sweeteners include, for example, stevia, coconut oil, sugar, saccharin, aspartame, sucralose, honey, and the like.

Generally, the lip balm may be prepared by heating the constituents of the lip balm base until the lip balm base is melted, dissolving the desired quantity of caffeine in a solvent, adding the dissolved caffeine to the melted lip balm base, and then allowing the lip balm base to cool.

In some embodiments, the method may further include, for example, pouring the molten lip balm base/caffeine mixture into a mold such as, for example, a tin or a lip balm tube.

In some embodiments, the method may further include adding one or more additives to the molten lip balm base. The additives may be added to the molten lip balm base before, after, or at the same time as the dissolved caffeine is added to the molten lip balm base.

The solvent used to dissolve the caffeine may be any suitable solvent or any suitable mixture of solvents. Caffeine is soluble to some extent in, for example, water, boiling water, alcohol, chloroform, pyrimidine, petroleum ether, benzene, acetone, pyrrole, tetrahydrofuran. The solvent may be selected on the basis of its suitability for use in a product that is intended for use in a manner that contemplates that constituents of the lip balm may be absorbed into the blood stream and/or ingested. In some cases, the solvent may be selected on the basis of the amount of caffeine that can be dissolved in a unit volume of the solvent. In other cases, a solvent may be selected on a basis that includes considerations other than merely the solubility of caffeine in the solvent. For example, one may elect to use an alcohol (e.g., ethanol)—or a mixture of an alcohol and another solvent (e.g., water)—because alcohols tend to evaporate easily, thereby permitting more of the solvent to evaporate after the caffeine is dissolved. In this way, the amount of solvent that remains in the lip balm after the molten lip balm base has cooled may be limited, if desired.

The solvent may include one or more solubilizing agents to increase the solubility of caffeine. For example, the solvent may include approximately 0.1% sodium benzoate.

In another aspect, the present invention provides a method of systemically delivering a dose of caffeine to a subject. Generally, the method includes topically administering to a mucous membrane surface of the subject a dose of caffeine effective to increase alertness in the subject.

The mucous membrane surface may be any mucous membrane surface of the subject to which a dose of a caffeine-containing formulation may be topically applied such as, for example, a mucous membrane surface of the lips and/or oral cavity. The mucous membrane surface of lip skin contains non-keratinized skin (i.e., the stratum corneum of the epidermis is extremely thin or completely absent). It also contains many capillaries near its translucent surface, thus giving rise to the red color of the so-called vermilion zone.

The caffeine may be provided in a formulation suitable for topical administration. The caffeine may be formulated as, for example, a solution, a suspension, an emulsion, or any form of mixture. The caffeine may be delivered in formulation with any pharmaceutically acceptable excipient, carrier, or vehicle. The formulation may be delivered in any conventional dosage form including but not limited to a wax, a stick, a cream, an ointment, an aerosol formulation, a non-aerosol spray, a gel, a lotion, and the like.

Topical administration of the caffeine-containing formulation may be by any suitable method including, for example, use of an applicator. A suitable applicator may be any device capable of applying a layer of the caffeine-containing formulation to a mucous membrane surface, including, for example, a finger, a brush, a spatula, a cotton swab, or a wipe. Alternatively, the caffeine-containing formulation may be applied directly from a container (e.g., a standard lip balm tube), without using an intermediary applicator.

Caffeine is considered an anti-cellulite agent for certain topical cosmetic products. However, topical application of such products involves applying the product to a keratinized skin surface affected by cellulite for a localized effect that is limited to the site of administration. As noted above, the epidermis of keratinized skin contains a stratum corneum that provides a barrier function that substantially limits molecules from passing into and out of the skin. Thus, the stratum corneum can reduce and even prevent absorption into the bloodstream of substances applied topically to keratinized skin.

In contrast, the method of the present invention involves topical administration of a caffeine-containing formulation to a mucous membrane surface such as may be found, for example, the in lip skin. The skin of the lip is different than typical (i.e., keratinized) skin: it lacks sweat glands and hair follicles, and the stratum corneum is extremely thin or completely absent. Therefore, caffeine topically applied to a mucous membrane surface may more readily pass through the skin, enter the bloodstream, and provide a systemic effect.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

Example 1

Lip balm base, sweetener, coloring, and flavoring were obtained from Le Melange Home Fragrances, Wellington, Fla. Approximately 453 grams (g) of lip balm base was heated over low heat until melted. Sweetener, flavoring, and coloring were added according to the manufacturer's instructions, then stirred until blended well.

630 mg of caffeine (Natural Food Supplements, Inc., Sherman Oaks, Calif.) was dissolved in approximately 30 milliliters (mL) of boiling water. Once dissolved, the caffeine was added to the molten lip balm base mixture, then stirred until blended well.

The molten mixture was poured into empty lip balm tubes and allowed to cool. Each tube contains approximately 4.3 g of lip balm that includes approximately 6.3 mg of caffeine.

Example 2

Lip balm base is melted and sweetener, flavoring, and coloring are added as described in Example 1.

20 g of caffeine is dissolved in approximately 40 mL of boiling water. Once dissolved, the caffeine is added to the molten lip balm base mixture.

The molten mixture is poured into empty lip balm tubes and allowed to cool. Each tube contains approximately 4.5 g of lip balm that includes approximately 200 mg of caffeine.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A lip balm comprising:
   a lip balm base; and
   caffeine, wherein a majority of the caffeine is dissolved in either the lip balm base or a solvent phase of an emulsion comprising the lip balm base.

2. The lip balm of claim 1 wherein the caffeine is present at a concentration of at least about 1.0 milligram per gram of lip balm base.

3. The lip balm of claim 2 wherein the caffeine concentration is at least about 1.4 milligrams per grain of lip balm base.

4. The lip balm of claim 3 wherein the caffeine concentration is at least about 22 milligrams per gram of lip balm base.

5. The lip balm of claim 4 wherein the caffeine concentration is at least about 400 milligrams per grain of lip balm base.

6. The lip balm of claim 1 further comprising at least one sweetener

7. The lip balm of claim 1 further comprising at least one colorant.

8. The lip balm of claim 1 further comprising at least one flavorant.

9. The lip balm of claim 1 further comprising at least one moisturizer.

10. The lip balm of claim 9 wherein the moisturizer comprises cocoa butter.

11. A method of making a lip balm comprising:
    melting a lip balm base;
    dissolving a majority of a quantity of caffeine in a solvent;
    adding the dissolved caffeine to the molten lip balm base; and
    allowing the lip balm base/caffeine mixture to cool.

12. The method of claim 11 wherein the solvent comprises water, an alcohol, or a mixture thereof.

13. The method of claim 11 wherein the quantity of caffeine is at least 80 milligrams per kilogram of molten lip balm base.

14. The method of claim 13 wherein the quantity of caffeine is at least 1.4 grams per kilogram of molten lip balm base.

15. The method of claim 14 wherein the quantity of caffeine is at least 22 grams per kilogram of molten lip balm base.

16. The method of claim 15 wherein the quantity of caffeine is at least 44 grams per kilogram of molten lip balm base.

17. The method of claim 16 wherein the quantity of caffeine is at least 400 grams per kilogram of molten lip balm base.

18. A method comprising:
    providing a lip balm comprising a lip balm base and dissolved caffeine wherein a majority of the caffeine is dissolved in either the lip balm base or a solvent phase of an emulsion comprising the lip balm base, and wherein topically administering the lip balm to a mucosal skin surface of a subject provides a dose of caffeine effective to increase alertness in the subject.

19. The method of claim 18 wherein the mucosal skin surface comprises lip skin.

20. The lip balm of claim 1 wherein the caffeine is dissolved in the lip balm base.

* * * * *